United States Patent
Holub et al.

(10) Patent No.: US 10,450,329 B2
(45) Date of Patent: Oct. 22, 2019

(54) PREPARATION OF DIFLUORO CHELATO BORATE SALTS

(71) Applicant: Gotion Inc., Fremont, CA (US)

(72) Inventors: Nicole Holub, Mannheim (DE); Juergen Herbel, Mannheim (DE)

(73) Assignee: Gotion Inc., Fremont, CA (US)

( * ) Notice: Subject to any disclaimer, the term of this patent is extended or adjusted under 35 U.S.C. 154(b) by 0 days.

(21) Appl. No.: 16/075,660

(22) PCT Filed: Jan. 27, 2017

(86) PCT No.: PCT/EP2017/051766
§ 371 (c)(1),
(2) Date: Aug. 6, 2018

(87) PCT Pub. No.: WO2017/133979
PCT Pub. Date: Aug. 10, 2017

(65) Prior Publication Data
US 2019/0048025 A1 Feb. 14, 2019

(30) Foreign Application Priority Data
Feb. 5, 2016 (EP) ..................................... 16154495

(51) Int. Cl.
| | | |
|---|---|---|
| *C07F 5/02* | (2006.01) |
| *H01G 11/62* | (2013.01) |
| *H01M 10/0525* | (2010.01) |
| *H01M 10/0568* | (2010.01) |
| *C07C 211/63* | (2006.01) |
| *C07D 213/20* | (2006.01) |
| *C07D 295/037* | (2006.01) |

(52) U.S. Cl.
CPC ............ *C07F 5/022* (2013.01); *C07C 211/63* (2013.01); *C07D 213/20* (2013.01); *C07D 295/037* (2013.01); *H01G 11/62* (2013.01); *H01M 10/0525* (2013.01); *H01M 10/0568* (2013.01); *H01M 2300/0025* (2013.01); *Y02E 60/13* (2013.01)

(58) Field of Classification Search
CPC ...................................................... C07F 5/022
USPC ........................................................ 546/347
See application file for complete search history.

(56) References Cited

U.S. PATENT DOCUMENTS

| | | |
|---|---|---|
| 6,783,896 B2 | 8/2004 | Tsujioka et al. |
| 2013/0026854 A1 | 1/2013 | Wang et al. |

FOREIGN PATENT DOCUMENTS

| | | |
|---|---|---|
| CN | 101643481 A | 2/2010 |
| CN | 103483367 A | 1/2014 |
| DE | 102006008020 A1 | 8/2007 |
| EP | 1308449 A2 | 5/2003 |
| WO | 2013072359 A1 | 5/2013 |

OTHER PUBLICATIONS

Journal of Power Sources; Crystal structure and physical properties of lithium difluoro (oxalato) borate (LiDFOB or LiFF2Ox); J. Allen, S. Han, P. Boyle, W. Henderson; 2011; 9737-9742.

*Primary Examiner* — Taofiq A Solola
(74) *Attorney, Agent, or Firm* — Young Basile Hanlon & MacFarlane, P.C.

(57) ABSTRACT

A process for preparing a difluoro chelato borate salt comprising an anion A of formula (I)

(I)

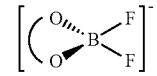

wherein

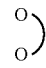

is a bidentate radical derived from a 1,2-, 1,3- or 1,4-diol, from a 1,2-, 1,3- or 1,4-dicarboxylic acid or from a 1,2-, 1,3- or 1,4-hydroxycarboxylic acid by abstracting the two H atoms of pairs of adjacent OH groups of the respective diol, hydroxycarboxylic acid or dicarboxylic acid. The process includes step (i) reacting (a) one or more BF3 sources; (b) a dihydric compound selected from 1,2-, 1,3- and 1,4-diols, 1,2-, 1,3- and 1,4-dicarboxylic acids, and 1,2-, 1,3- and 1,4-hydroxycarboxylic acids; (c) one or more second boron sources which do not contain F; and (d) one or more proton acceptors.

9 Claims, No Drawings

PREPARATION OF DIFLUORO CHELATO BORATE SALTS

CROSS-REFERENCE TO RELATED APPLICATION(S)

This application is a 371 application of International Application No. PCT/EP2017/051766, filed on Jan. 27, 2017, which claims priority to European Patent Application No. 16154495.2, filed on Feb. 5, 2016, the content of which is hereby incorporated by reference in its entirety.

DETAILED DESCRIPTION

The present disclosure relates to a preparation process for difluoro chelato borate salts.

Difluoro chelato borate salts like lithium and ammonium difluoro oxalato borates are used in electrolyte compositions for electrochemical cells, see e.g. U.S. Pat. No. 6,783,896 B2 and WO 2013/026854 A1. The synthesis of the difluoro borate anions usually involves a fluorine and boron containing compound, e.g. tetrafluoroborate salts or $BF_3$ compounds.

U.S. Pat. No. 6,783,896 B2 describes the synthesis of lithium difluoro oxalato borate by reacting $LiBF_4$ with a lithium alkoxide followed by the addition of oxalic acid. Besides the desired lithium difluoro oxalato borate LiF is formed which has to be removed from the product.

J. L. Allen et al, Journal of Power Sources 196 (2011), pages 9737 to 9742 discloses the preparation of difluoro oxalato borate by direct reaction of excess boron trifluoride diethyl etherate ($BF_3$-ether) with lithium oxalate.

DE 10 2006 008 020 A1 relates to ionic liquids for use in electrochemical applications and describes the preparation of tetraethylammonium difluoro oxalato borate by reaction of tretraethylammonium tetrafluoroborate, oxalic acid and $SiCl_4$. In addition to the desired difluoro oxalato borate the by-products $SiF_4$ and HCl are formed.

All these preparation processes have in common that not all of the fluorine contained in the $BF_4$ salt or $BF_3$ compound used in the synthesis are converted or incorporated into the difluoro chelato borate anion and/or that an excess of a fluorine and boron containing educt has to be used. This leads to an unfavorable and inefficient loss of fluorine. Additionally, the fluorine containing by-products have to be removed from the product.

It was an object of the present disclosure to provide a process for preparing difluoro chelato borates like difluoro oxalato borate wherein the fluorine containing educt is efficiently used, the generation of fluorine containing by-products is reduced and the overall yield of difluoro chelato borate should be high. It was also an object to use educts, which are comparatively cheap and easily accessible and to avoid the use of intermediate products like lithium alkoxides, tetrafluoroborate salts and $SiCl_4$, which require additional synthesis steps and may be difficult to handle in some cases.

These objects are achieved by a process for preparing a difluoro chelato borate salt comprising an anion A of formula (I)

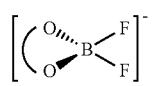

(I)

wherein

is a bidentate radical derived from a 1,2-, 1,3- or 1,4-diol, from a 1,2-, 1,3- or 1,4-dicarboxylic acid or from a 1,2-, 1,3- or 1,4-hydroxycarboxylic acid by abstracting the two H atoms of pairs of adjacent OH groups of the respective diol, hydroxycarboxylic acid or dicarboxylic acid;

comprising step (i) reacting
one or more $BF_3$ sources;
a dihydric compound selected from 1,2-, 1,3- and 1,4-diols, 1,2-, 1,3- and 1,4-dicarboxylic acids, and 1,2-, 1,3- and 1,4-hydroxycarboxylic acids;
one or more second boron sources which do not contain F; and
one or more proton acceptor.

Due to the addition of the second boron source, which does not contain F, most of the fluorine provided by the $BF_3$ source is converted into difluoro chelato borate and the amount of fluorine containing by-products is reduced. The educts used are comparatively cheap and easy to obtain and the use of educts like lithium alkoxides and $SiCl_4$ is avoided. The process does not require the presence of any additional sources for F-atoms like LiF. The preparation process is simple and does not require special equipment or special measures like the use of inert gas. The yields of difluoro chelato borates obtainable by the present process are high and purification steps are avoided.

In the following the disclosure is described in detail.

The present process relates to the preparation of difluoro chelato borate salts comprising an anion A of formula (I)

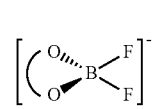

(I)

wherein

is independently at each occurrence a bidentate radical derived from a 1,2-, 1,3- or 1,4-diol, from a 1,2-, 1,3- or 1,4-dicarboxylic acid or from a 1,2-, 1,3- or 1,4-hydroxycarboxylic acid by abstracting the two H atoms of pairs of adjacent OH groups of the respective diol, hydroxycarboxylic acid or dicarboxylic acid in 1,2-, 1,3- or 1,4-position.

The term "adjacent OH groups" means the two hydroxyl groups present in the respective functional groups in 1,2-, 1,3- or 1,4-position, i.e. the two OH-groups present in the two carboxylic acid groups of a 1,2-, 1,3- or 1,4-dicarboxylic acid, the two OH-groups present in a 1,2-, 1,3- or 1,4-diol or the two OH-groups present in the carboxylic acid group and the alcoholic OH-group of a 1,2-, 1,3- or 1,4-hydroxycarboxylic acid.

Suited 1,2-, 1,3- and 1,4-diols from which the bidentate radical is derived may be aliphatic or aromatic and are optionally substituted by one or more F and/or by at least one straight or branched non-fluorinated, partly fluorinated or fully fluorinated $C_1$-$C_4$ alkyl group. They may be selected, e.g., from ethane-1,2-diol, propane-1,2-diol, butane-1,2-diol, propane-1,3-diol, butan-1,3-diol, butan-1,4-diol, cyclohexyl-trans-1,2-diol, 1,2-dihydroxybenzene, biphenyl-2,2'-diol, and naphthalene-2,3-diol which are optionally are substituted by one or more F and/or by at least one straight or branched non-fluorinated, partly fluorinated or fully fluorinated $C_1$-$C_4$ alkyl group. An example of a fluorinated diol is 1,1,2,2-tetra(trifluoromethyl)-1,2-ethane diol.

"Fully fluorinated $C_1$-$C_4$ alkyl group" means, that all H-atoms of the alkyl group are substituted by F. "Partially fluorinated $C_1$-$C_4$ alkyl group" means that at least one but not all H-atoms of the alkyl group are substituted by F.

Suited 1,2-, 1,3- and 1,4-dicarboxlic acids from which the bidentate radical is derived may be aliphatic or aromatic, for example oxalic acid, malonic acid (propane-1,3-dicarboxylic acid), phthalic acid or isophthalic acid, preferred is oxalic acid. The 1,2-, 1,3- and 1,4-dicarboxlic acids are optionally substituted by one or more F and/or by at least one straight or branched non-fluorinated, partly fluorinated or fully fluorinated $C_1$-$C_4$ alkyl group.

Suited 1,2-, 1,3- and 1,4-hydroxycarboxylic acids from which the bidentate radical is derived may be aliphatic or aromatic and are optionally substituted by one or more F and/or by at least one straight or branched non-fluorinated, partly fluorinated or fully fluorinated $C_1$-$C_4$ alkyl group. Examples of 1,2-, 1,3- and 1,4-hydroxycarboxylic acids are salicylic acid, tetrahydro salicylic acid, malic acid, and 2-hydroxy acetic acid, which are optionally substituted by one or more F and/or by at least one straight or branched non-fluorinated, partly fluorinated or fully fluorinated $C_1$-$C_4$ alkyl group. An example of a fluorinated 1,2-hydroxycarboxylic acid is 2,2-bis(trifluoromethyl)-2-hydroxy-acetic acid.

Preferably

is a bidentate radical derived from 1,2- or 1,3-hydroxycarboxylic acids, 1,2- or 1,3-dicarboxlic acids, or 1,2- or 1,3-diols, more preferred

is a bidentate radical derived from 1,2-hydroxycarboxylic acids, 1,2-dicarboxlic acids, or 1,2-diols, e.g.

is oxalic acid, salicylic acid, or phthalic acid, in particular preferred is oxalic acid.

For the preparation of the difluoro chelato borate anion components (a) to (d) are used. As component (a) one or more $BF_3$ sources are used. Every compound which is capable to provide $BF_3$ for the reaction may be used. $BF_3$ itself is a strong Lewis acid which forms easily adducts with a large number of electron donors including ethers, alcohols, ketones, amines, phosphines, arsines, thiols, and selenides. Such adducts are capable to provide $BF_3$ for the reaction. The $BF_3$ source (a) may for example be selected from $BF_3$, $BF_3$ hydrate, $BF_3$ etherates, $BF_3$-alcohol adducts, $BF_3$-acetonitril adduct, $BF_3$-acetic acid adduct, and $BF_3$-amine adducts. Preferably the one or more $BF_3$ source (a) is selected from $BF_3$ hydrate, $BF_3$-alcohol adducts, and $BF_3$ etherates, more preferred the $BF_3$ source (a) is selected from $BF_3$ hydrate and $BF_3$-alcohol adducts, in particular preferred the $BF_3$ source (a) is selected from $BF_3$ hydrate and $BF_3$-methanol adducts.

As component (b) a dihydric compound selected from 1,2-, 1,3- and 1,4-diols, 1,2-, 1,3- and 1,4-dicarboxylic acids, and 1,2-, 1,3- and 1,4-hydroxycarboxylic acids is used. The dihydric compound (b) is selected according to the desired difluoro chelato borate anion A, i.e. the dihydric compound (b) is selected from the dihydric compounds from which the bidentate radical

of the anion A of formula (I) is derived. The dihydric compound (b) is selected from the 1,2-, 1,3- and 1,4-diols, 1,2-, 1,3- and 1,4-dicarboxylic acids, and 1,2-, 1,3- and 1,4-hydroxycarboxylic acids described above. Preferably the dihydric compound (b) is selected from 1,2- and 1,3-hydroxycarboxylic acids, 1,2- and 1,3-dicarboxlic acids, and 1,2- and 1,3-diols, more preferred the dihydric compound (b) is selected from 1,2-hydroxycarboxylic acids, 1,2-dicarboxlic acids, and 1,2-diols, e.g. from oxalic acid, salicylic acid, and phthalic acid, in particular preferred the dihydric compound (b) is oxalic acid.

As component (c) one or more second boron sources which do not contain F are used in the preparation process. During the reaction in step (i) the $BF_3$ source is converted into the difluoro chelato borate anion and superfluous fluorine is released. The second boron source, which does not contain F, uptakes the superfluous fluorine released from the $BF_3$ source during the reaction in step (i) and thereby is converted into a difluoro chelato borate anion A, too. This leads to an efficient use and high conversion of the fluorine containing educt. The second boron source may for example be selected from boric acid ($B(OH)_3$), $B(OC_1$-$C_6$ alkyl$)_3$, $B(OC_5$-$C_7$ (hetero)aryl$)_3$, and ammonium and alkali metal salts of borate complexes of the dihydric compound used as component (b). Such borate complexes are bis(chelato) borates of formula (II)

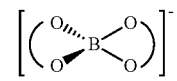

(II)

wherein the bidentate radical

is defined as described above or described as preferred.

The alkali metal salts may be selected from the lithium, sodium, potassium or caesium salts. The ammonium salts may be a cation [NR"$_4$]$^+$ wherein R" is selected independently from each other from H, optionally substituted C$_1$-C$_{20}$ alkyl, C$_2$-C$_{20}$ alkenyl, C$_2$-C$_{20}$ alkynyl, C$_5$-C$_{12}$ (hetero)aryl, and C$_6$-C$_{30}$ (hetero)aralkyl, wherein one or more CH$_2$ groups of alkyl, alkenyl, alkynyl and (hetero)aralkyl which are not directly bound to the N-atom may be replaced by O, 1,2-epoxyethylene, cyclopropylene, OSO$_2$, SO$_2$O, OC(O), C(O)O, OC(O)O, or OC(O)C(O)O;

or wherein two R" are linked and jointly selected from a 4- to 5-membered hydrocarbon group forming together with the central N-atom a five- or six-membered heterocycle which may substituted by one or more substituents selected from C$_1$-C$_{10}$ alkyl, and wherein one or more members of the 4- to 5-membered hydrocarbon group may be replaced by one or more O, S or NR'";

R'" is selected from H, C$_1$-C$_{10}$ alkyl, C$_2$-C$_{10}$ alkenyl, C$_2$-C$_{10}$ alkynyl, C$_6$-C$_{12}$ aryl, and C$_7$-C$_{24}$ aralkyl, which may be substituted by one or more groups selected from F, cyclopropyl, 1,2-epoxyethyl, and sulfonate, and wherein one or more CH$_2$ groups of alkyl, alkenyl, alkynyl and aralkyl which are not directly bound to the N-atom may be replaced by O, 1,2-epoxyethylene, cyclopropylene, OSO$_2$ or SO$_2$O.

Preferred are ammonium cations [NR"$_4$]$^+$ wherein R" is selected independently from each other from H, optionally substituted C$_1$-C$_{20}$ alkyl, C$_5$-C$_{12}$ (hetero)aryl, and C$_6$-C$_{30}$ (hetero)aralkyl, wherein one or more CH$_2$ groups of alkyl and (hetero)aralkyl which are not directly bound to the N-atom may be replaced by O, 1,2-epoxyethylene, cyclopropylene, OSO$_2$, SO$_2$O, OC(O), C(O)O, OC(O)O, or OC(O)C(O)O;

or wherein two R" are linked and jointly selected from a 4- to 5-membered hydrocarbon group forming together with the central N-atom a five- or six-membered heterocycle which may substituted by one or more substituents selected from C$_1$-C$_{10}$ alkyl, and wherein one or more members of the 4- to 5-membered hydrocarbon group may be replaced by one or more O, S or NR'";

R'" is selected from H and C$_1$-C$_{10}$ alkyl.

More preferred are ammonium cations [NR"$_4$]$^+$ wherein R" is selected independently from each other from H, optionally substituted C$_1$-C$_{10}$ alkyl, C$_5$-C$_{12}$ (hetero)aryl, and C$_6$-C$_{18}$ (hetero)aralkyl;

or wherein two R" are linked and jointly selected from a 4- to 5-membered hydrocarbon group forming together with the central N-atom a five- or six-membered heterocycle which may substituted by one or more substituents selected from C$_1$-C$_{10}$ alkyl, and wherein one or more members of the 4- to 5-membered hydrocarbon group may be replaced by one or more O, S or NR'";

R'" is selected from H and C$_1$-C$_{10}$ alkyl.

In particular preferred are ammonium cations [NR"$_4$]$^+$ wherein R" is selected independently from each other from H, and C$_1$ to C$_6$ alkyl; or wherein two R" are linked and jointly selected from a 4- to 5-membered hydrocarbon group forming together with the central N-atom a five- or six-membered heterocycle which may substituted by one or more substituents selected from C$_1$-C$_{10}$ alkyl, and wherein one or more members of the 4- to 5-membered hydrocarbon group may be replaced by one or more O, S or NR'"; and R'" is selected from H and C$_1$-C$_{10}$ alkyl.

Examples of such alkali metal and ammonium salts of borate complexes of the dihydric compound used as component (b) are lithium bis(oxalato) borate and triethylammonium bis(oxalato) borate. Examples of B(OC$_1$-C$_6$ alkyl)$_3$ and B(OC$_5$-C$_7$ (hetero)aryl)$_3$ are trimethoxy borane, triethoxy borane, triisopropoxy borane, tri-n-propoxy borane, and triphenoxy borane. It is possible to use one, two or more different compounds as second boron source (c), e.g. boric acid and a lithium salt of the respective bis(chelato) borate. Preferably the one or more second boron source (c) is selected from boric acid and lithium and ammonium bis (chelato) borates. In particular preferred is boric acid.

In case the dihydric compound (b) is oxalic acid, the second boron source (c) which does not contain F is preferably selected from boric acid, trimethoxy borane, lithium bis(oxalato) borate, triethylammonium bis(oxalato) borate, and mixtures thereof, more preferred the second boron source (c) is boric acid.

Usually the BF$_3$ source (a) and the second boron source (c) are used in step (i) in a molar ratio ranging from 1.5:1 to 2.5:1, referred to boron. It is preferred to keep the molar ratio of BF$_3$ source (a) and second boron source (c) around 2:1, which is the optimal stoichiometric ratio. The molar ratio may for example range from 1.5:1 to 2.5:1, preferably from 1.8:1 to 2.2:1 and most preferred from 1.9:1 to 2.1:1, referred to boron, respectively. It is in particular preferred that no excess of the BF$_3$ source (a) in respect to the second boron source (c) is used, i.e. that the molar ratio of BF$_3$ source (a) and second boron source (c) is at maximum 2:1.

Preferably the F-atoms present in the resulting difluoro chelato borate salts stem essentially from the BF$_3$ source (a). But it might be possible that an additional source for F-atoms is present. An additional source for F-atoms means a compound which provides F-atoms to the reaction without providing any BF$_3$ unit to the reaction. An example for an additional source for F-atoms is LiF. Usually the total content of additional sources for F-atoms is less than 50 mol.-% based on the total amount of BF$_3$-source (a), preferably less than 20 mol.-%, more preferred less than 10 mol.-%, even more preferred less than 5 mol.-% and most preferred less than 1 mol.-%, based on the total amount of BF$_3$-source (a).

Additionally one or more proton acceptors (d) are used in the reaction of step (i). During the formation of the difluoro chelato borate the dihydric compound (b) releases two protons per molecule. The proton acceptor (d) takes up at least part of these protons. Depending on the compounds selected as component (c) more or less of proton acceptor (d) is required. E.g. boric acid used as component (c) releases one hydroxide group per molecule. This hydroxide group can uptake one of the two protons released by the dihydric compound (b) and only the remaining one of the two protons has to be taken up by the one or more proton acceptor (d) per molecule of dihydric compound. In case a second boron source (c) like lithium bis(oxalato) borate is used, which does not release any protons during the reaction, the one or more proton acceptors (d) will uptake both protons released by the dihydric compound (b). The one or more proton acceptors (d) used in the reaction are usually selected to be different from the compounds used as components (a), (b) and (c).

The proton acceptor (d) may for example be selected from ammonia, organic amines, NH$_4$OH, organic ammonium hydroxides, and nitrogen containing aromatic heterocycles. It is possible to use one, two or more compounds as proton acceptor (d).

Examples of organic amines and organic ammonium hydroxides are organic amines NR$^1$R$^2$R$^3$ and organic ammonium hydroxides [NR$^1$R$^2$R$^3$R$^4$]OH
wherein
R$^1$, R$^2$, R$^3$, and R$^4$ are selected independently from each other from H, optionally substituted C$_1$-C$_{20}$ alkyl, C$_2$-C$_{20}$ alkenyl, C$_2$-C$_{20}$ alkynyl, C$_6$-C$_{12}$ (hetero)aryl, and C$_6$-C$_{30}$ (hetero)aralkyl, wherein one or more CH$_2$ groups of alkyl, alkenyl, alkynyl and (hetero)aralkyl which are not directly bound to the N-atom may be replaced by O, 1,2-epoxyethylene, cyclopropylene, $OSO_2$, $SO_2O$, $OC(O)$, $C(O)O$, $OC(O)O$, or $OC(O)C(O)O$;

or wherein $R^1$ and $R^2$ are linked and jointly selected from a 4- to 5-membered hydrocarbon group forming together with the central N-atom a five- or six-membered heterocycle which may substituted by one or more substituents selected from $C_1$-$C_{10}$ alkyl, and wherein one or more members of the 4- to 5-membered hydrocarbon group may be replaced by one or more O, S or NR';

R' is selected from H, $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the N-atom may be replaced by O, 1,2-epoxyethylene, cyclopropylene, $OSO_2$ or $SO_2O$; and wherein at least one of $R^1$, $R^2$, and $R^3$ is not H.

The term "$C_1$-$C_{20}$ alkyl" as used herein means a straight or branched saturated hydrocarbon group with 1 to 20 carbon atoms having one free valence and includes, e.g., methyl, ethyl, n-propyl, isopropyl, n-butyl, sec-butyl, isobutyl, tert-butyl, n-pentyl, iso-pentyl, 2,2-dimethylpropyl, n-hexyl, iso-hexyl, 2-ethyl hexyl, n-heptyl, iso-heptyl, n-octyl, iso-octyl, n-nonyl, n-decyl and the like. Preferred are $C_1$-$C_{10}$ alkyl groups, more preferred are $C_1$-$C_6$ alkyl groups, even more preferred are $C_1$-$C_4$ alkyl groups, and most preferred are methyl, ethyl, and iso-propyl.

The term "$C_2$-$C_{20}$ alkenyl" as used herein refers to an unsaturated straight or branched hydrocarbon group with 2 to 20 carbon atoms having one free valence. Unsaturated means that the alkenyl group contains at least one C—C double bond. $C_2$-$C_{20}$ alkenyl includes for example ethenyl, 1-propenyl, 2-propenyl, 1-n-butenyl, 2-n-butenyl, iso-butenyl, 1-pentenyl, 1-hexenyl, 1-heptenyl, 1-octenyl, 1-nonenyl, 1-decenyl and the like. Preferred are $C_2$-$C_{10}$ alkenyl groups, more preferred are $C_2$-$C_6$ alkenyl groups, even more preferred are $C_2$-$C_4$ alkenyl groups and in particular preferred are ethenyl and 1-propen-3-yl (allyl).

The term "$C_2$-$C_{20}$ alkynyl" as used herein refers to an unsaturated straight or branched hydrocarbon group with 2 to 20 carbon atoms having one free valence, wherein the hydrocarbon group contains at least one C—C triple bond. $C_2$-$C_{20}$ alkynyl includes for example ethynyl, 1-propynyl, 2-propynyl, 1-n-butynyl, 2-n-butynyl, iso-butinyl, 1-pentynyl, 1-hexynyl, -heptynyl, 1-octynyl, 1-nonynyl, 1-decynyl and the like. Preferred are $C_2$-$C_{10}$ alkynyl, more preferred are $C_2$-$C_6$ alkynyl, even more preferred are $C_2$-$C_4$ alkynyl, in particular preferred are ethynyl and 1-propyn-3-yl (propargyl).

The term "$C_5$-$C_{12}$ (hetero)aryl" as used herein denotes an aromatic 5- to 12-membered hydrocarbon cycle or condensed cycles having one free valence wherein one or more of the C-atoms of the aromatic cycle(s) may be replaced independently from each other by a heteroatom selected from N, S, O and P. Examples of $C_6$-$C_{12}$ (hetero)aryl are phenyl, naphtyl, pyrrolyl, furanyl, thiophenyl, pyridinyl, pyranyl, and thiopyranyl. Preferred is phenyl.

The term "$C_6$-$C_{30}$ (hetero)aralkyl" as used herein denotes an aromatic or heteroaromatic 5- to 12-membered aromatic hydrocarbon cycle or condensed aromatic or heteroaromatic cycles substituted by one or more $C_1$-$C_6$ alkyl. The $C_6$-$C_{24}$ (hetero)aralkyl group contains in total 6 to 30 C-atoms and has one free valence. The free valence may be located at the aromatic cycle or at a $C_1$-$C_6$ alkyl group, i.e. $C_6$-$C_{24}$ aralkyl group may be bound via the aromatic part or via the alkyl part of the (hetero)aralkyl group. Examples of $C_6$-$C_{24}$ (hetero)aralkyl are methylphenyl, 1,2-dimethylphenyl, 1,3-dimethylphenyl, 1,4-dimethylphenyl, ethylphenyl, 2-i-propylphenyl, 2-methylfuryl, 2-methylpyridiyl, and the like.

The term "sulfonate" as used herein means the groups —$S(O)_2O$—$R^{iv}$ or —$OS(O)_2$—$R^{iv}$ wherein $R^{iv}$ is selected from $C_1$-$C_{10}$ alkyl, preferably from $C_1$-$C_6$ alkyl and more preferred from $C_1$-$C_4$ alkyl.

The term "cyclopropylene" as used herein means the group derived from cyclopropane molecule having two free valences at two adjacent C-atoms:

the asterisks denote the two free valences.

The term "1,2-epoxyethyl" as used herein means an oxirane cycle having one free valence:

the asterisk denotes the free valence.

The term "1,2-epoxyethylene" as used herein means an oxirane cycle having two free valences at the two adjacent C-atoms:

the asterisks denote the free valences.

The term "optionally substituted $C_1$-$C_{20}$ alkyl, $C_2$-$C_{20}$ alkenyl, $C_2$-$C_{20}$ alkynyl, $C_5$-$C_{12}$ (hetero)aryl, and $C_6$-$C_{30}$ (hetero)aralkyl" means that each of the alkyl, alkenyl, alkynyl, (hetero)aryl and (hetero)aralkyl group may be substituted, e.g. by groups selected from F, cyclopropyl, 1,2-epoxyethyl, and sulfonate.

Preferred organic amines and organic ammonium hydroxides for use as proton acceptor (d) are organic amines $NR^1R^2R^3$ and organic ammonium hydroxides $[NR^1R^2R^3R^4]$OH wherein $R^1$, $R^2$, $R^3$, and $R^4$ are selected independently from each other from H and $C_1$-$C_{20}$ alkyl or wherein $R^1$ and $R^2$ are linked and jointly selected from a 4- to 5-membered hydrocarbon group forming together with the central N-atom a five- or six-membered heterocycle which may substituted by one or more substituents selected from $C_1$-$C_{10}$ alkyl, and wherein one or more members of the 4- to 5-membered hydrocarbon group may be replaced by one or more O, S or NR'; R' is selected from H and $C_1$-$C_{10}$ alkyl; and wherein at least one of $R^1$, $R^2$, and $R^3$ is not H.

More preferred organic amines and organic ammonium hydroxides are organic amines $NR^1R^2R^3$ and organic ammonium hydroxides $[NR^1R^2R^3R^4]$OH wherein $R^1$, $R^2$, $R^3$, and $R^4$ are selected independently from each other from H and $C_1$-$C_{10}$ alkyl or wherein $R^1$ and $R^2$ are linked and jointly selected from a 4- to 5-membered hydrocarbon group forming together with the central N-atom a five- or six-membered heterocycle which may substituted by one or more substituents selected from $C_1$-$C_{10}$ alkyl; and wherein at least one of $R^1$, $R^2$, and $R^3$ is not H.

In particular preferred organic amines and organic ammonium hydroxides are organic amines $NR^1R^2R^3$ and organic ammonium hydroxides [NR$^1$R$^2$R$^3$R$^4$]OH wherein R$^1$, R$^2$, R$^3$, and R$^4$ are selected independently from each other from H and C$_1$-C$_6$ alkyl and wherein at least one of R$^1$, R$^2$, and R$^3$ is not H.

Examples of organic amines and organic ammonium hydroxides are methyl amine, ethyl amine, isopropyl amine, dimethyl amine, diethyl amine, diisopropyl amine, trimethyl amine, triethyl amine, triisopropyl amine, ethyl dimethyl amine, diethylmethyl amine, isopropyl dimethyl amine, diisopropyl methyl amine, diethyl isopropyl amine, ethyl diisopropyl amine, tetramethyl ammonium hydroxide, tetraethyl ammonium hydroxide, isopropyl ammonium hydroxide, and N-methylpyrrolidine In particular preferred are isopropyl amine and triethyl amine.

It is also possible to use nitrogen containing aromatic heterocycles as proton acceptor (d). Nitrogen containing aromatic heterocycles may for examples be selected from pyridine, pyrimidine, pyrrol, pyrazol, and imidazole.

Preferably, the proton acceptor (d) is selected from NH$_4$OH and the organic amines and organic ammonium hydroxides as described above and as described as preferred, more preferred from the organic amines as described above and as described as preferred.

During the reaction in step (i) volatile reaction products may be formed, e.g. water from the reaction of boric acid used as second boron source (c) or from ammonium hydroxide used as proton acceptor (d) or ethers or alcohols from the respective BF$_3$-adducts used as BF$_3$ source (a). Such volatile reaction products may be removed during and/or after step (i), e.g. by distillation. It is advantageous to remove the water formed to accelerate the reaction, e.g. by distillation or by adding drying agents like molecular sieves or magnesium sulfate.

Depending on the compounds (a) to (d) used it may be advantageous that an organic solvent or solvent mixture (e) is present in the reaction mixture of step (i), e.g. in case one or more compounds (a) to (d) are solid at the reaction temperature. Any solvent or solvent mixture suitable may be used, e.g. the solvent or solvent mixture (e) may be selected from water, C$_1$ to C$_6$ alcohols, di-C$_1$ to C$_6$ alkylethers, C$_1$ to C$_4$ carboxylic acids, C$_1$ to C$_4$ alkylesters, di-C$_1$ to C$_4$ alkyl carbonates, acetonitrile, aromatic hydrocarbons, aliphatic hydrocarbons, and C$_1$ to C$_4$ ketones and mixtures thereof.

The term "C$_1$ to C$_6$ alcohol" means an alcohol containing 1 to 6 C-atoms and at least one alcoholic OH-group. Examples of C$_1$ to C$_6$ alcohols include methanol, ethanol, i-propanol, n-propanol, n-butanol, i-butanol, sec-butanol, tert-butanol etc. More preferred are methanol, ethanol and i-propanol, most preferred is methanol.

Examples of di-C$_1$-C$_6$-alkylethers are dimethylether, ethylmethylether, diethylether, diisopropylether, di-n-butylether, and methyl-tert-butylether, preferred is methyl-tert-butylether.

The term "C$_1$ to C$_4$ carboxylic acid C$_1$ to C$_4$ alkylester" means an ester of a carboxylic acid containing 1 to 4 C-atoms and an alcohol containing 1 to 4 C-atoms. Examples of C$_1$ to C$_4$ carboxylic acid C$_1$ to C$_4$ alkylester are methyl formiate, ethyl formiate, methyl acetate, ethyl acetate, methyl proprionate and methyl butanoate. Preferred are methyl acetate and ethyl acetate.

Di-C$_1$ to C$_4$ alkyl carbonates are acyclic organic carbonates, wherein each C$_1$ to C$_4$ alkyl group is selected independently from each other. Examples are diethyl carbonate (DEC), ethyl methyl carbonate (EMC), dimethyl carbonate (DMC), and methylpropyl carbonate. Preferred are diethyl carbonate (DEC), ethyl methyl carbonate (EMC), and dimethyl carbonate (DMC).

Examples of C$_1$ to C$_4$ ketones are acetone and ethylmethylketone. Preferred is acetone.

Aromatic hydrocarbons are e.g. benzene and C$_6$ to C$_{14}$ aralkyl compounds like toluene, ethylbenzene, isopropylbenzene, and xylene.

Aliphatic hydrocarbons are e.g. C$_5$ to C$_{20}$ branched and linear alkanes like n-hexane and n-heptane and C$_5$ to C$_7$ cycloalkanes like cyclohexane.

The solvent or solvent mixture (e) is preferably selected from solvents, which are miscible with water and more preferred from solvents forming an azeotrope with water. The use of a solvent or solvent mixture (e) which forms an azeotrope with water is in particular beneficial if water is a by-product in reaction step (i) since it facilitates removal of the water formed and accelerates the reaction.

Preferably the solvent or solvent mixture (e) comprises at least one solvent selected from acetone, acetonitrile, aromatic hydrocarbons like benzene, toluene, ethylbenzene, isopropylbenzene, and xylene, and C$_1$ to C$_6$ alcohols like methanol, ethanol, iso-propanol, n-propanol, n-butanol, iso-butanol, sec-butanol, tert-butanol etc. More preferred the solvent or solvent mixture (e) comprises at least one solvent selected from acetone, acetonitrile, toluene, and methanol, most preferred is methanol. Even more preferred the at least one solvent (e) is selected from acetone, acetonitrile, toluene, and methanol, most preferred the at least one solvent (e) is methanol.

The components (a) to (d) and (e) if present and optionally further components are usually mixed together. It might be beneficial to add the BF$_3$ source after a mixture of the other components in a reaction vessel was provided to avoid problems with possible exothermic decomposition or outgassing of BF$_3$.

Usually the reaction of step (i) is carried out at elevated temperature, i.e. above 25° C. Preferably the reaction is carried out in a temperature range from 50 to 200° C., more preferred in temperature range from 75 to 175° C.

A preferred embodiment of the disclosure is a process for preparing a difluoro chelato borate salt containing an anion A of formula (I) wherein step (i) comprises reacting (a) one or more compounds selected from BF$_3$, BF$_3$ hydrate, BF$_3$ etherates, and BF$_3$-alcohol adducts, preferably BF$_3$ hydrate;

(b) oxalic acid, salicylic acid or phthalic acid, preferably oxalic acid;

(c) boric acid or a mixture of boric acid and one or more bis(chelato) borate salts selected from lithium bis(chelato) borates and [NR"$_4$]$^+$bis(chelato) borates, wherein R" is selected independently from each other from H, and C$_1$ to C$_6$ alkyl, or wherein two R" are linked and jointly selected from a 4- to 5-membered hydrocarbon group forming together with the central N-atom a five- or six-membered heterocycle which may substituted by one or more substituents selected from C$_1$-C$_{10}$ alkyl, and wherein one or more members of the 4- to 5-membered hydrocarbon group may be replaced by one or more O, S or NR'''; and R''' is selected from H and C$_1$-C$_{10}$ alkyl;

and wherein the chelato group is derived from the compound used as component (b); and (d) at least one proton acceptor selected from ammonia, nitrogen containing aromatic heterocycles, NH$_4$OH, and organic amines NR$^1$R$^2$R$^3$ and organic ammonium hydroxides [NR$^1$R$^2$R$^3$R$^4$]OH wherein R$^1$, R$^2$, R$^3$, and R$^4$ are selected independently from each other from H and C$_1$-C$_{10}$ alkyl or wherein R$^1$ and R$^2$ are linked and jointly selected from a 4- to 5-membered hydrocarbon group forming together with the central N-atom a five- or six-membered heterocycle which may substituted by one or more substituents selected from $C_1$-$C_{10}$ alkyl; and wherein at least one of $R^1$, $R^2$, and $R^3$ is not H;
(e) optionally a solvent or solvent mixture comprising one or more solvents selected from acetone, acetonitrile, aromatic hydrocarbons, and $C_1$ to $C_6$ alcohols.

Another preferred embodiment of the present disclosure is a process for preparing a difluoro oxalato borate salt wherein step (i) comprises reacting
(a) one or more compounds selected from $BF_3$, $BF_3$ hydrate, $BF_3$ etherates, and $BF_3$-alcohol adducts, preferably $BF_3$ hydrate;
(b) oxalic acid;
(c) one or more compounds selected boric acid, lithium bis(oxalato) borate and $[NR''_4]^+$ bis(oxalato) borate wherein R" is selected independently from each other from H and $C_1$ to $C_6$ alkyl; or wherein two R are linked and jointly selected from a 4- to 5-membered hydrocarbon group forming together with the central N-atom a five- or six-membered heterocycle which may substituted by one or more substituents selected from $C_1$-$C_{10}$ alkyl, and wherein one or more members of the 4- to 5-membered hydrocarbon group may be replaced by one or more O, S or NR'''; and R''' is selected from H and $C_1$-$C_{10}$ alkyl; preferably boric acid;
(d) at least one proton acceptor selected from ammonia, nitrogen containing aromatic heterocycles, and organic amines $NR^1R^2R^3$ and organic ammonium hydroxides $[NR^1R^2R^3R^4]OH$ wherein $R^1$, $R^2$, $R^3$, and $R^4$ are selected independently from each other from H and $C_1$-$C_{10}$ alkyl or wherein $R^1$ and $R^2$ are linked and jointly selected from a 4- to 5-membered hydrocarbon group forming together with the central N-atom a five- or six-membered heterocycle which may substituted by one or more substituents selected from $C_1$-$C_{10}$ alkyl; and wherein at least one of $R^1$, $R^2$, and $R^3$ is not H.
(e) optionally a solvent or solvent mixture comprising one or more solvents selected from acetone, acetonitrile, aromatic hydrocarbons, and $C_1$ to $C_6$ alcohols.

The difluoro chelato borate salt prepared according to the present process comprises an anion A of formula (I) and a cation. The cation may also be referred to as K and is preferably a monovalent cation carrying the charge of +1. K may be selected from organic ammonium and phosphonium cations as described below, preferably K is selected from cations $K^1$ and $K^2$ as described below and as described as preferred.

The proton acceptor (d) may have a second function within the reaction of step (i), it may also provide the cation for the difluoro chelato borate anion formed. This means it is possible to determine the cation of the difluoro chelato borate salt prepared in step (i) by selecting the proton acceptor (d). For example, if the proton acceptor (d) is selected from ammonia, organic amines, organic ammonium hydroxides, $NH_4OH$, and nitrogen containing aromatic heterocycles, the proton acceptor (d) provides an ammonium cation during the reaction of step (i). Ammonia, organic amines and nitrogen containing aromatic heterocycles take up a proton and form an ammonium cation in situ. In case of $NH_4OH$ and the organic ammonium hydroxides, the hydroxide anion takes up the proton yielding water and the organic ammonium cation or $NH_4^+$.

A further object of the present disclosure is therefore a process for preparing a difluoro chelato borate salt wherein the cation of the difluoroborate salt comprising an anion A stems from the proton acceptor (d) used in step (i). This means the cation is generated from the proton acceptor (d) used in the preparation step (i), preferably during the reaction step (i). In case the cation K of the difluoroborate salt comprising an anion A stems from the proton acceptor (d) used in step (i) the cation is also denoted $K^1$. $K^1$ preferably has the charge +1. The cation $K^1$ is preferably selected from $NH_4$, $[NR^1R^2R^3H]^+$, protonated nitrogen containing aromatic heterocycles, and $[NR^1R^2R^3R^4]^+$ wherein $R^1$, $R^2$, $R^3$, and $R^4$ are defined as described above or described as being preferred. More preferred $K^1$ is selected from $NH_4$, $[NR^1R^2R^3H]^+$, and $[NR^1R^2R^3R^4]^+$ wherein $R^1$, $R^2$, $R^3$, and $R^4$ are defined as described above or described as being preferred.

It is also possible to add a further salt in step (i) as source of the cation K of the difluoro chelato borate salt to be prepared. The further salt is also denoted component (f). Usually the cation $K^2$ of the further salt (f) is different from the cation generated by the proton acceptor (d) during the reaction. Adding a further salt (f) is advantageous if the desired cation K of the difluoro chelato borate salt cannot be easily generated from the proton acceptor (d). This may be the case if the desired cation K is a fully substituted ammonium cation and the ammonium cannot or only with additional efforts be provided as ammonium hydroxide or if there is no precursor of the desired cation which can be used as proton acceptor (d). Sometimes it may be cheaper to provide the cation of the desired difluoro chelato borate salt by adding a further salt as component (f) as source of the desired cation.

The present disclosure includes also a process for preparing a difluoro chelato borate salt KA comprising an anion A of formula (I) as described above comprising step (i) reacting
(a) one or more $BF_3$ sources;
(b) a dihydric compound selected from 1,2-, 1,3- and 1,4-diols, 1,2-, 1,3- and 1,4-dicarboxylic acids, and 1,2-, 1,3- and 1,4-hydroxycarboxylic acids;
(c) one or more second boron sources which do not contain F;
(d) one or more proton acceptors; and
(e) optionally a solvent or solvent mixture; and
(f) a further salt as source of cation K.

Components (a) to (e) are defined as described above and step (i) is carried out as described above. The further salt (f) is usually added in the stoichiometric required amount or in an amount yielding an excess of the difluoro chelato borate anion formed theoretically in respect to the amount of anion present in further salt (f), preferably in an amount yielding an excess of the difluoro chelato borate anion formed theoretically. E.g. in case K is a monovalent cation the further salt (f) is added in an amount providing a molar ratio of further salt (f) and boron contained in the $BF_3$ source (a) of around 1:1. This ratio yields a molar ratio of anion present in the further salt (f) to difluoro chelato borate anion theoretically formed during the reaction of 1:1.5. The molar ratio of further salt (f) and boron contained in the $BF_3$ source (a) may for example range from 1.5:1 to 0.5:1, preferably from 1.3:1 to 0.6:1 and most preferred from 1.1:1 to 0.7:1, referred to the molar ratio of further salt (f) and boron contained in the $BF_3$ source (a), respectively.

In case a further salt (f) is present, step (i) is preferably carried out in the presence of a solvent or solvent mixture (e). Preferably the further salt (f) used as source of cation K is an organic ammonium or phosphonium salt $K^2A^1$ as defined below. The desired difluoro chelato borate salt $K^2A$ is usually separated after step (i).

According to a preferred embodiment step (i) is carried out in the presence of a solvent or solvent mixture (e) and an organic ammonium or phosphonium salt $K^2A^1$ and after step (i) the difluoro chelato borate salt $K^2A$ is separated, wherein $K^2$ is selected from $[XR^5R^6R^7R^8]^+$;

X is N or P;

$R^5$, $R^6$, $R^7$, and $R^8$ are selected independently from each other from H, optionally substituted $C_1$-$C_{20}$ alkyl, $C_2$-$C_{20}$ alkenyl, $C_2$-$C_{20}$ alkynyl, $C_5$-$C_{12}$ (hetero)aryl, and $C_6$-$C_{30}$ (hetero)aralkyl, wherein one or more $CH_2$ groups of alkyl, alkenyl, alkynyl and (hetero)aralkyl which are not directly bound to the X-atom may be replaced by O, 1,2-epoxyethylene, cyclopropylene, $OSO_2$, $SO_2O$, OC(O), C(O)O, OC(O)O, or OC(O)C(O)O;

or wherein $R^5$ and $R^6$ are linked and jointly selected from a 4- to 5-membered hydrocarbon group forming together with the central X-atom a five- or six-membered heterocycle which may substituted by one or more substituents selected from $C_1$-$C_{10}$ alkyl, and wherein one or more members of the 4- to 5-membered hydrocarbon group may be replaced by one or more O, S or NR";

R" is selected from H, $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the N-atom may be replaced by O, 1,2-epoxyethylene, cyclopropylene, $OSO_2$ or $SO_2O$; and $A^1$ is selected from $[R^9$—$SO_3]^-$, $Cl^-$, $Br^-$, and $I^-$, wherein $R^9$ is selected from $C_1$-$C_{20}$ alkyl, $C_2$-$C_{20}$ alkenyl, $C_2$-$C_{20}$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the $SO_3^-$ group may be replaced by O, 1,2-epoxyethylene, cyclopropylene, $OSO_2$ or $SO_2O$.

X is N or P; preferably X is N.

Preferably $R^5$, $R^6$, $R^7$, and $R^8$ are selected independently from each other from $C_1$-$C_{10}$ alkyl, $C_2$-$C_{10}$ alkenyl, $C_2$-$C_{10}$ alkynyl, $C_5$-$C_7$ (hetero)aryl, and $C_6$-$C_{18}$ (hetero)aralkyl, which may be substituted by one or more groups selected from F, cyclopropyl, 1,2-epoxyethyl, and sulfonate, and wherein one or more $CH_2$ groups of alkyl, alkenyl, alkynyl and (hetero)aralkyl which are not directly bound to the X-atom may be replaced by O, 1,2-epoxyethylene, cyclopropylene, $OSO_2$ or $SO_2O$; or $R^5$ and $R^6$ are linked and jointly selected from a 4- to 5-membered hydrocarbon group forming together with the central X-atom a five- or six-membered heterocycle which may be substituted by one or more substituents selected from $C_1$-$C_{10}$ alkyl, and wherein one or more members of the 4- to 5-membered hydrocarbon group may be replaced by one or more O, S or NR".

The five- or six-membered heterocycle formed by $R^5$ and $R^6$ and the central X-atom may be selected for example from

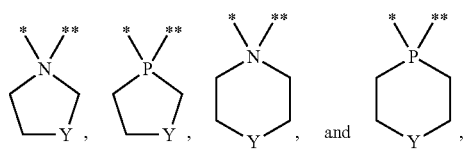

wherein Y is $CH_2$, O, S or NR" and the asterisks denote the bonds to $R^7$ and $R^8$, respectively. Examples of five- or six-membered heterocycles formed by $R^5$ and $R^6$ and the central X-atom are pyrrolidine, piperidine, and morpholine.

If $R^5$ and $R^6$ are not linked, $R^5$ and $R^6$ are preferably selected independently from each other from $C_1$-$C_6$ alkyl, $C_2$-$C_6$ alkenyl, $C_2$-$C_6$ alkynyl, $C_5$-$C_7$ (hetero)aryl, and $C_6$-$C_{18}$ (hetero)aralkyl, and more preferred from $C_1$-$C_4$ alkyl, $C_2$-$C_4$ alkenyl, $C_2$-$C_4$ alkynyl, $C_5$-$C_7$ (hetero)aryl, and $C_6$-$C_{14}$ (hetero)aralkyl, and most preferred from $C_1$-$C_4$ alkyl, $C_2$-$C_4$ alkenyl, $C_2$-$C_4$ alkynyl, wherein alkyl, alkenyl, alkynyl, aryl and aralkyl may be substituted one or more groups selected from F, cyclopropyl, 1,2-epoxyethyl and sulfonate, and wherein one or more $CH_2$ group of alkyl, alkenyl, alkynyl and aralkyl which are not directly bound to the X-atom may be replaced by O, 1,2-epoxyethylene, cyclopropylene, $OSO_2$ or $SO_2O$.

If $R^5$ and $R^6$ are linked they are preferably jointly selected from a 4-membered hydrocarbon group forming together with the central X-atom a five-membered heterocycle which may be substituted by one or more substituents selected from F and optionally fluorinated $C_1$-$C_{10}$ alkyl, preferably from F and optionally fluorinated $C_1$-$C_4$ alkyl, and wherein one or more members of the 4-membered hydrocarbon group may be replaced by O, S or NR". The preferred five-membered heterocycle formed by $R^5$ and $R^6$ and the central X-atom is pyrrolidine.

$R^5$ and $R^6$ are preferably linked and jointly selected from a 4- to 5-membered hydrocarbon group forming together with the central X-atom a five- or six-membered heterocycle, which may be substituted by one or more substituents selected from F and optionally fluorinated $C_1$-$C_{10}$ alkyl, and wherein one or more members of the 4- to 5-membered hydrocarbon group may be replaced by O, S or NR", more preferred they are selected from a 4-membered hydrocarbon group forming together with the central X-atom a five-membered heterocycle, which may be substituted by one or more substituents selected from F and optionally fluorinated $C_1$-$C_{10}$ alkyl, and wherein one or more members of the 4-membered hydrocarbon group may be replaced by O, S or NR".

$R^7$ and $R^8$ are preferably selected from optionally substituted $C_1$-$C_{10}$ alkyl, $C_2$-$C_{10}$ alkenyl, $C_2$-$C_{10}$ alkynyl, $C_5$-$C_{12}$ (hetero)aryl, and $C_6$-$C_{24}$ (hetero)aralkyl, more preferred from $C_1$-$C_6$ alkyl, $C_2$-$C_6$ alkenyl, $C_2$-$C_6$ alkynyl, $C_5$-$C_7$ (hetero)aryl, and $C_6$-$C_{18}$ (hetero)aralkyl, even more preferred from $C_1$-$C_6$ alkyl, $C_2$-$C_6$ alkenyl, and $C_2$-$C_6$ alkynyl, wherein one or more $CH_2$ groups of alkyl, alkenyl, alkynyl and (hetero)aralkyl which are not directly bound to the X-atom may be replaced by O, 1,2-epoxyethylene, cyclopropylene, $OSO_2$, $SO_2O$, OC(O), C(O)O, OC(O)O, or OC(O)C(O)O.

It is preferred if at least one of $R^7$ and $R^8$ comprises an optionally substituted alkyl, alkenyl, alkynyl and (hetero)aralkyl group wherein at least one $CH_2$ group which is not directly bound to the X-atom is replaced by $OSO_2$ or $SO_2O$.

It is preferred that $R^8$ is L-$OSO_2R^{8a}$, i.e. preferred cations $K^2$ are cations of formula (II)

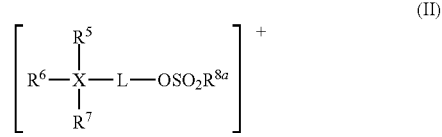

wherein $R^5$, $R^6$, and $R^7$ are selected as defined above or as preferred,

L is a —$(CH_2)_n$— chain wherein one or more $CH_2$ groups of the —$(CH_2)_n$— chain which are not directly bound to the X-atom or the $OSO_2$ group may be replaced by O and wherein a C—C single bond between two adjacent $CH_2$ groups of the —$(CH_2)_n$-chain may be replaced by a C—C double bond or a C—C triple bond;

n is an integer from 1 to 8;

$R^{8a}$ is selected from $C_1$-$C_{18}$ alkyl, $C_2$-$C_{18}$ alkenyl, $C_2$-$C_{18}$ alkynyl, $C_5$-$C_{12}$ (hetero)aryl, and $C_6$-$C_{22}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the $OSO_2$ group may be replaced by O, 1,2-epoxyethylene, cyclopropylene, $OSO_2$ or $SO_2O$.

n is an integer selected from 1, 2, 3, 4, 5, 6, 7, and 8, preferably n is 1, 2, 3 or 4, more preferred n is 2, 3 or 4.

Preferably L is a non-substituted alkylene chain with n being selected as defined above.

$R^{8a}$ is selected from $C_1$-$C_{18}$ alkyl, $C_2$-$C_{18}$ alkenyl, $C_2$-$C_{18}$ alkynyl, $C_5$-$C_{12}$ (hetero)aryl, and $C_5$-$C_{22}$ (hetero)aralkyl, preferably $R^{4a}$ is selected from $C_1$-$C_{10}$ alkyl, $C_2$-$C_{10}$ alkenyl, $C_2$-$C_{10}$ alkynyl, $C_5$-$C_7$ (hetero)aryl, and $C_6$-$C_{18}$ (hetero)aralkyl, and more preferred $C_1$-$C_6$ alkyl, $C_2$-$C_6$ alkenyl, $C_2$-$C_6$ alkynyl, $C_5$-$C_7$ (hetero)aryl, and $C_6$-$C_{18}$ (hetero)aralkyl, which may be substituted by one or more groups selected from F, cyclopropyl, 1,2-epoxyethyl, and sulfonate, and wherein one or more $CH_2$ groups of alkyl, alkenyl, alkynyl and (hetero)aralkyl which are not directly bound to the $OSO_2$ group may be replaced by O, 1,2-epoxyethylene, cyclopropylene, $OSO_2$ or $SO_2O$; in particular preferred $R^{8a}$ is selected from methyl, ethyl, propyl, ethenyl, 1-propen-3-yl, ethynyl, and 1-propyn-3-yl.

An example for a cation $K^2$ is 1-methyl-1-(2-((methylsulfonyl)oxy)ethyl)-pyrrolidinium.

The anion $A^1$ is an organic or inorganic anion and may be selected from organic sulfonates, $Cl^-$, $Br^-$, and $I^-$. The organic sulfonates may be selected from sulfonates of formula $[R^9—SO_3]^-$ wherein $R^9$ is selected from $C_1$-$C_{20}$ alkyl, $C_2$-$C_{20}$ alkenyl, $C_2$-$C_{20}$ alkynyl, $C_5$-$C_{12}$ (hetero)aryl, and $C_6$-$C_{24}$ (hetero)aralkyl, and preferred from $C_1$-$C_6$ alkyl, $C_2$-$C_6$ alkenyl, $C_2$-$C_6$ alkynyl, $C_5$-$C_7$ (hetero) aryl, and $C_6$-$C_{18}$ (hetero)aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the $OSO_2$ group may be replaced by O, 1,2-epoxyethylene, cyclopropylene, $OSO_2$ or $SO_2O$; in particular preferred $R^9$ is selected from methyl, ethyl, propyl, ethenyl, 1-propen-3-yl ethynyl and 1-propyn-3-yl. An example of an organic sulfonate which can be used as $A^1$ is $[CH_3—SO_3]^-$. In case $A^1$ is $[R^9—SO_3]^-$ no halide anions are used which have to be removed carefully if compound KA is used in lithium ion batteries, since halides have a detrimental effect on the life time of lithium ion batteries.

Especially preferred $A^1$ is an anion selected from $[R^9—SO_3]^-$ and K is an anion of formula (II) wherein $R^{8a}$ and $R^9$ are same. Such compounds wherein $R^{8a}$ and $R^9$ are same are easily prepared in one step as described below. The use of symmetrical educts for the preparation of $KA^1$ which are substituted twice by the same substituent $SOR^{8a}$ in comparison to educts which are unsymmetrically substituted is simpler. The synthesis of $K^2A^1$ from educts substituted by halogen and $SOR^{8a}$ is more complicated and expensive.

Preferably the further salt (f) is selected from salt of formula $K^2A^1$ wherein $K^2$ is a cation of formula (II), wherein X is N, $R^5$ and $R^6$ form together with the central X-atom a five-membered heterocycle, $R^7$ and $R^{8a}$ are selected from $C_1$ to $C_6$ alkyl, and L is a —$(CH_2)_n$— chain with n=1, 2, 3 or 4; and $A^1$ is an anion selected from $[R^9—SO_3]^-$ wherein $R^9$ is selected from $C_1$-$C_6$ alkyl.

An example of $K^2A^1$ is 1-methyl-1-(2-((methylsulfonyl)oxy)ethyl)-pyrrolidinium methansulfonate.

After step (i) the desired difluoro chelato borate salt is separated from the reaction mixture. The separation of the desired difluoro chelato borate salt is also named step (ii). The difluoro chelato borate salt may be separated from the reaction mixture by precipitation. Precipitation may be induced by adding a non-solvent for the difluoro borate salt, by cooling the reaction mixture obtained in step (i) or by removing solvent(s) present in the reaction mixture by distillation until the crystallization of the difluoro chelato borate salt begins.

The disclosure is illustrated by the examples which follow, which do not, however, restrict the invention.

I.) Preparation of triethylammonium difluoro(oxalatoborate)

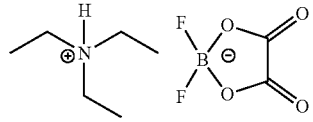

Example 1

38 g oxalic acid dihydrate, 6 g boric acid and 30 g triethylamine were mixed with 150 mL acetonitrile. 21 g Bortrifluorid-dihydrate was added and the reaction mixture was heated to 120-130° C., while volatile components were removed by distillation. The residue was further dried for 2 h at 120° C. and 10 mbar. Upon cooling, triethylammonium difluoro(oxalatoborate) was obtained as colorless, solidified melt. Quantitative F-NMR showed a purity of 92%, together with the corresponding tetrafluoro borate salt (2%) and bis(oxalatoborate) salt in 6%.

Example 2

38 g oxalic acid dihydrate, 6 g boric acid and 30 g triethylamine were mixed with 150 mL acetone. 21 g Bortrifluorid-dihydrate was added and the reaction mixture was heated to 120-130° C., while volatile components were removed by distillation. The residue was further dried for 2 h at 120° C. and 10 mbar. Upon cooling, triethylammonium difluoro(oxalatoborate) was obtained as colorless, solidified melt. Quantitative F-NMR showed a purity of 93%, together with the corresponding tetrafluoro borate salt (3%) and bis(oxalatoborate) salt in 4%.

Example 3

38 g oxalic acid dihydrate, 6 g boric acid and 30 g triethylamine were mixed with 150 mL methanol. 21 g Bortrifluorid-dihydrate was added and the reaction mixture was heated to 120-130° C., while volatile components were removed by distillation. The residue was further dried for 2 h at 120° C. and 10 mbar. Upon cooling, triethylammonium difluoro(oxalatoborate) was obtained as colorless, solidified melt. Quantitative F-NMR showed a purity of 88%, together with the corresponding tetrafluoro borate salt (6%) and bis(oxalatoborate) salt in 6%.

Example 4

Triethylammonium difluoro(oxalatoborate) was prepared according to example 3. Crystallization from a mixture of acetone and methyl-tert-butyl-ether resulted in isolation of colorless, crystalline material in 40% yield. Quantitative F-NMR showed a purity of 100%.

$^1$H NMR (CD$_3$CN, 400 MHz) δ (ppm)=1.23 (t, 9H), 2.20 (br, s, 1H), 3.15 (quar, 6H). $^{19}$F NMR (CD$_3$CN, 376 MHz) δ=−154 ppm. $^{11}$B NMR (CD$_3$CN, 128 MHz) δ=3.0 ppm. Melting Point: 55° C.

Example 5

38 g oxalic acid dihydrate, 6 g boric acid and 30 g triethylamine were mixed with 150 mL methanol. 26 g Bortrifluorid-methanol adduct was added and the reaction mixture was heated to 120-130° C., while volatile components were removed by distillation. The residue was further dried for 2 h at 120° C. and 10 mbar. Upon cooling, triethylammonium difluoro(oxalatoborate) was obtained as colorless, solidified melt. Quantitative F-NMR showed a purity of 84%, together with the corresponding tetrafluoro borate salt (7%) and bis(oxalatoborate) salt in 9%.

Example 6

19 g oxalic acid dihydrate, 43 g triethyammonium bis (oxalatoborate) and 30 g triethylamine were mixed with 150 mL acetonitrile. 31 g Bortrifluorid-dihydrate was added and the reaction mixture was heated to 120-130° C., while volatile components were removed by distillation. The residue was further dried for 2 h at 120° C. and 10 mbar. Upon cooling, triethylammonium difluoro(oxalatoborate) was obtained as colorless, solidified melt. Quantitative F-NMR showed a purity of 90%, together with the corresponding tetrafluoro borate salt (4%) and bis(oxalatoborate) salt in 6%. $^{19}$F NMR (CD$_3$CN, 376 MHz) δ (ppm)=−154 (BF$_2$), −150 (BF$_4$). $^{11}$B NMR (CD$_3$CN, 128 MHz) δ (ppm)=−1.2 (BF$_4$), 3.0 (BF$_2$), 7.5 (B).

II.) Preparation of ethyl-di(isopropyl)ammonium difluoro(oxalatoborate)

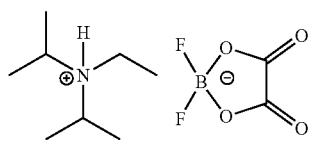

Example 7

38 g oxalic acid dihydrate, 6 g boric acid and 38 g ethyl-di(isopropyl)amine were mixed with 150 mL methanol. 21 g Bortrifluorid-dihydrate was added and the reaction mixture was heated to 120-130° C., while volatile components were removed by distillation. The residue was further dried for 2 h at 120° C. and 10 mbar. Upon cooling, ethyl-di(isopropyl)ammonium difluoro(oxalatoborate) was obtained as yellowish, solidified melt in 97% yield. Quantitative F-NMR showed a purity of 87%, together with the corresponding tetrafluoro borate salt (6%) and bis(oxalatoborate) salt in 7%.

$^1$H NMR (MeOD, 400 MHz) δ (ppm)=1.32-1.48 (m, 15H), 3.22 (quar, 2H), 3.60-3.71 (m, 2H). $^{19}$F NMR (MeOD, 376 MHz) δ=−154 ppm. $^{11}$B NMR (MeOD, 128 MHz) δ=3.0 ppm. Melting Point: 229° C.

III.) Preparation of ethyl-di(methyl)ammonium difluoro(oxalatoborate)

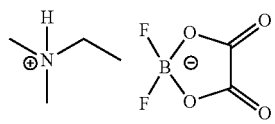

Example 8

38 g oxalic acid dihydrate, 6 g boric acid and 22 g ethyl-di(methyl)amine were mixed with 150 mL methanol. 21 g Bortrifluorid-dihydrate was added and the reaction mixture was heated to 120-130° C., while volatile components were removed by distillation. The residue was further dried for 2 h at 120° C. and 10 mbar. Upon cooling, ethyl-di(methyl)ammonium difluoro(oxalatoborate) was obtained as yellowish, solidified melt in 96% yield. Quantitative F-NMR showed a purity of 89%, together with the corresponding tetrafluoro borate salt (4%) and bis(oxalatoborate) salt in 7%.

$^1$H NMR (MeOD, 400 MHz) δ (ppm)=1.36 (t, 3H), 2.87 (s, 6H), 3.18 (quar, 2H). $^{19}$F NMR (MeOD, 376 MHz) δ=−154 ppm. $^{11}$B NMR (MeOD, 128 MHz) δ=3.0 ppm. Melting Point: 48° C.

IV.) Preparation of isopropylammonium difluoro(oxalatoborate)

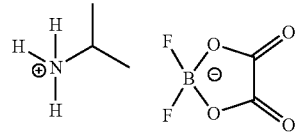

Example 9

38 g oxalic acid dihydrate, 6 g boric acid and 18 g isopropylamine were mixed with 150 mL methanol. 21 g Bortrifluorid-dihydrate was added and the reaction mixture was heated to 120-130° C., while volatile components were removed by distillation. The residue was further dried for 2 h at 120° C. and 10 mbar. Upon cooling, isopropylammonium difluoro(oxalatoborate) was obtained as colorless, solidified melt in 89% yield. Quantitative F-NMR showed a purity of 90%, together with the corresponding tetrafluoro borate salt (2%) and bis(oxalatoborate) salt in 8%.

¹H NMR (MeOD, 400 MHz) δ (ppm)=1.39 (d, 6H), 3.38-3.52 (m, 1H). ¹⁹F NMR (MeOD, 376 MHz) δ=−154 ppm. ¹¹B NMR (MeOD, 128 MHz) δ=3.0 ppm. Melting Point: 38° C.

V.) Preparation of tetraethylammonium difluoro(oxalatoborate)

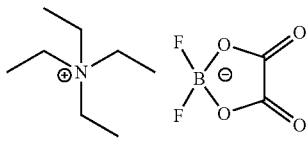

Example 10

38 g oxalic acid dihydrate, 6 g boric acid and 44 g tetraethylammonium hydroxide were mixed with 150 mL methanol. 21 g Bortrifluorid-dihydrate was added and the reaction mixture was heated to 120-130° C., while volatile components were removed by distillation. The residue was further dried for 2 h at 120° C. and 10 mbar. Upon cooling, tetraethylammonium difluoro(oxalatoborate) was obtained as colorless, solidified melt in 75% yield. Quantitative F-NMR showed a purity of 92%, together with the corresponding tetrafluoro borate salt (4%) and bis(oxalatoborate) salt in 4%.

¹H NMR (MeOD, 400 MHz) δ (ppm)=1.20 (t, 12H), 3.17 (quar, 8H). ¹⁹F NMR (MeOD, 376 MHz) δ=−154 ppm. ¹¹B NMR (MeOD, 128 MHz) δ=3.0 ppm. Melting Point: 118° C.

VI.) Preparation of N-methylpyrrolidinium difluoro(oxalatoborate)

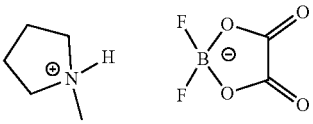

Example 11

38 g oxalic acid dihydrate, 6 g boric acid and 26 g N-methylpyrrolidine were mixed with 150 mL methanol. 21 g Bortrifluorid-dihydrate was added and the reaction mixture was heated to 120-130° C., while volatile components were removed by distillation. The residue was further dried for 2 h at 120° C. and 10 mbar. Upon cooling, N-methylpyrrolidinium difluoro(oxalatoborate) was obtained as dark red, solidified melt in 95% yield. Quantitative F-NMR showed a purity of 86%, together with the corresponding tetrafluoro borate salt (6%) and bis(oxalatoborate) salt in 8%.

¹H NMR (MeOD, 400 MHz) δ (ppm)=1.82-2.03 (m, 2H), 2.05-2.23 (m, 2H), 2.89 (d, 3H), 2.95-3.06 (m, 2H), 3.60-3.74 (m, 2H). ¹⁹F NMR (MeOD, 376 MHz) δ=−154 ppm. ¹¹B NMR (MeOD, 128 MHz) δ=3.0 ppm. Melting Point: 232° C.

VII.) Preparation of pyridinium difluoro(oxalatoborate)

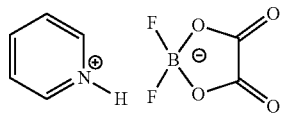

Example 12

38 g oxalic acid dihydrate, 6 g boric acid and 24 g pyridin were mixed with 150 mL methanol. 21 g Bortrifluorid-dihydrate was added and the reaction mixture was heated to 120-130° C., while volatile components were removed by distillation. The residue was further dried for 2 h at 120° C. and 10 mbar. Upon cooling, pyridinium difluoro(oxalatoborate) was obtained as colorless, solidified melt in 85% yield. Quantitative F-NMR showed a purity of 90%, together with the corresponding tetrafluoro borate salt (3%) and bis(oxalatoborate) salt in 7%.

¹H NMR (MeOD, 400 MHz) δ (ppm)=8.02-8.14 (m, 2H), 8.58-8.69 (m, 1H), 8.82-8.90 (m, 2H). ¹⁹F NMR (MeOD, 376 MHz) δ=−154 ppm. ¹¹B NMR (MeOD, 128 MHz) δ=3.0 ppm. Melting Point: 90° C.

VIII.) Preparation of 1-methyl-1-(2-((methylsulfonyl)oxy)ethyl)-pyrrolidinium difluoro(oxalatoborate)

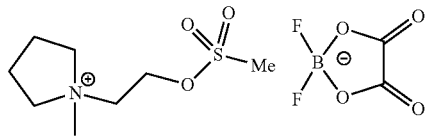

Example 13

A solution of 346 g 1-methyl-1-(2-((methylsulfonyl)oxy)ethyl)-pyrrolidinium methansulfonate in methanol was charged to a reactor at room temperature. 35 g Boric acid, 216 g oxalic acid dihydrate, 173 g triethylamine and 118 g bortrifluorid dihydrate were added under stirring and the reaction mixture was heated to 70° C. After cooling to 20° C., seed crystals of 1-methyl-1-(2-((methylsulfonyl)oxy)ethyl)-pyrrolidinium difluoro(oxalatoborate) were added and stirring was continued for additional 12 h at 0° C. The suspension was filtered and the residue sequentially washed with portions of cold methanol. 1-methyl-1-(2-((methylsulfonyl)oxy)ethyl)-pyrrolidinium difluoro(oxalatoborate) was obtained as colorless solid in 8% yield.

Example 14

A solution of 346 g 1-methyl-1-(2-((methylsulfonyl)oxy)ethyl)-pyrrolidinium methansulfonate in methanol was charged to a reactor at room temperature. 24 g Boric acid, 144 g oxalic acid dihydrate, 115 g triethylamine and 79 g bortrifluorid dihydrate were added under stirring and the reaction mixture was heated to 120-130° C., while volatile components were removed by distillation. The residue was further dried for 2 h at 120° C. and 10 mbar. After cooling to 25° C., methanol was added, followed by seed crystals of 1-methyl-1-(2-((methylsulfonyl)oxy)ethyl)-pyrrolidinium difluoro(oxalatoborate) and additional stirring for 12 h at 0° C. The suspension was filtered and the residue sequentially washed with portions of cold methanol. 1-methyl-1-(2-((methylsulfonyl)oxy)ethyl)-pyrrolidinium difluoro(oxalatoborate) was obtained as colorless solid in 45% yield.

Example 15

A solution of 346 g 1-methyl-1-(2-((methylsulfonyl)oxy) ethyl)-pyrrolidinium methansulfonate in methanol was charged to a reactor at room temperature. 35 g Boric acid, 216 g oxalic acid dihydrate, 173 g triethylamine and 118 g bortrifluorid dihydrate were added under stirring and the reaction mixture was heated to 120-130° C., while volatile components were removed by distillation. The residue was further dried for 2 h at 120° C. and 10 mbar. After cooling to 25° C., methanol was added, followed by seed crystals of 1-methyl-1-(2-((methylsulfonyl)oxy)ethyl)-pyrrolidinium difluoro(oxalatoborate) and additional stirring for 12 h at 0° C. The suspension was filtered and the residue sequentially washed with portions of cold methanol. 1-methyl-1-(2-((methylsulfonyl)oxy)ethyl)-pyrrolidinium difluoro(oxalatoborate) was obtained as colorless solid in 51% yield.

The invention claimed is:

1. A process for preparing a difluoro chelato borate salt comprising an anion A of formula (I)

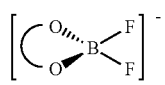

(I)

wherein

is a bidentate radical derived from a 1,2-, 1,3- or 1,4-diol, from a 1,2-, 1,3- or 1,4-dicarboxylic acid or from a 1,2-, 1,3- or 1,4-hydroxycarboxylic acid by abstracting the two H atoms of pairs of adjacent OH groups of the respective diol, hydroxycarboxylic acid or dicarboxylic acid;
 comprising, in the presence of an ammonium salt or a phosphonium salt, step (i) reacting
 (a) one or more $BF_3$ sources selected from bortrifluorid-dihydrate and bortrifluorid-methanol;
 (b) a dihydric compound selected from 1,2-, 1,3- and 1,4-diols, 1,2-, 1,3- and 1,4-dicarboxylic acids, and 1,2-, 1,3- and 1,4-hydroxycarboxylic acids, wherein the dihydric compound (b) is selected from oxalic acid, salicylic acid, and phthalic acid;
 (c) one or more second boron sources which do not contain F; and
 (d) one or more proton acceptors;
 wherein the $BF_3$ source (a) and the second boron source (c) are used in step (i) in a molar ratio ranging from 1.5:1 to 2.5:1, referred to boron;
 wherein the second boron source (c) is selected from boric acid, $B(OC_1-C_6$ alkyl$)_3$, $B(OC_5-C_7$ (hetero)aryl$)_3$, and ammonium and alkali metal salts of borate complexes of the dihydric compound used as component (b);
 wherein the proton acceptor (d) is selected from organic amines $NR^1R^2R^3$, $NH_4OH$, and organic ammonium hydroxides $[NR^1R^2R^3R^4]OH$
 wherein
 $R^1$, $R^2$, $R^3$, and $R^4$ are selected independently from each other from H, optionally substituted $C_1-C_{20}$ alkyl, $C_2-C_{20}$ alkenyl, $C_2-C_{20}$ alkynyl, $C_5-C_{12}$ (hetero)aryl, and $C_6-C_{30}$ (hetero)aralkyl, wherein one or more $CH_2$ groups of alkyl, alkenyl, alkynyl and (hetero)aralkyl which are not directly bound to the N-atom may be replaced by O, 1,2-epoxyethylene, cyclopropylene, $OSO_2$, $SO_2O$, $OC(O)$, $C(O)O$, $OC(O)O$, or $OC(O)C(O)O$;
 or wherein $R^1$ and $R^2$ are linked and jointly selected from a 4- to 5-membered hydrocarbon group forming together with the central N-atom a five- or six-membered heterocycle which may substituted by one or more substituents selected from $C_1-C_{10}$ alkyl, and wherein one or more members of the 4- to 5-membered hydrocarbon group may be replaced by one or more O, S or NR';
 R' is selected from H, $C_1-C_{10}$ alkyl, $C_2-C_{10}$ alkenyl, $C_2-C_{10}$ alkynyl, $C_6-C_{12}$ aryl, and $C_7-C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the N-atom may be replaced by O, 1,2-epoxyethylene, cyclopropylene, $OSO_2$ or $SO_2O$; and
 wherein at least one of $R^1$, $R^2$, and $R^3$ is not H.

2. The process according to claim 1, wherein the total content of additional sources for F-atoms is less than 50 mol.-% based on the total amount of $BF_3$-source (a).

3. The process according to claim 1, wherein the volatile reaction products are removed during and/or after step (i).

4. The process according to claim 1, wherein the dihydric compound (b) is selected from 1,2-diols, 1,2-dicarboxylic acids, and 1,2-hydroxycarboxylic acids.

5. The process according to claim 1, wherein the proton acceptor (d) is selected from ammonia, organic amines, organic ammonium hydroxides, $NH_4OH$, and nitrogen containing aromatic heterocycles.

6. The process according to claim 1, wherein the proton acceptor (d) is selected from organic amines $NR^1R^2R^3$ and organic ammonium hydroxides $[NR^1R^2R^3R^4]OH$
 wherein
 $R^1$, $R^2$, $R^3$, and $R^4$ are selected independently from each other from H and optionally substituted $C_1-C_{20}$ alkyl or wherein $R^1$ and $R^2$ are linked and jointly selected from a 4- to 5-membered hydrocarbon group forming together with the central N-atom a five- or six-membered heterocycle which may substituted by one or more substituents selected from $C_1-C_{10}$ alkyl, and wherein one or more member of the 4- to 5-membered hydrocarbon group may be replaced by one or more O, S or NR';
 R' is selected from H and $C_1-C_{10}$ alkyl; and
 wherein at least one of $R^1$, $R^2$, and $R^3$ is not H.

7. The process according to claim 1, wherein the proton acceptor (d) is a nitrogen containing aromatic heterocycle selected from pyridine, pyrimidine, pyrrol, pyrazol, and imidazole.

8. The process according to claim 1, wherein the cation of the difluoro chelato borate salt comprising an anion A stems from the proton acceptor (d) used in step (i).

9. The process according to claim 1, wherein step (i) is carried out in the presence of a solvent or solvent mixture (e), wherein the ammonium salt or the phosphonium salt is a source of the cation of the difluoro chelato borate salt comprising an anion A.

* * * * *